United States Patent [19]

Schachet et al.

[11] 3,993,067
[45] Nov. 23, 1976

[54] AUTOTRANSFUSION DEVICE

[75] Inventors: Eli Schachet, St. Louis, Mo.; Eugene E. Weilbacher, Columbia, Ill.

[73] Assignee: Sherwood Medical Industries Inc., St. Louis, Mo.

[22] Filed: Apr. 24, 1975

[21] Appl. No.: 571,112

[52] U.S. Cl............................................. 128/214 C
[51] Int. Cl.².......................................... A61M 5/00
[58] Field of Search......... 128/214 R, 214 C, 214.2, 128/276; 210/DIG. 23

[56] References Cited
UNITED STATES PATENTS

| | | | |
|---|---|---|---|
| 3,021,841 | 2/1962 | Burke | 128/214 C |
| 3,492,991 | 2/1970 | Dyer, Jr. | 128/214 R |
| 3,536,451 | 10/1970 | Ludwin | 128/214 R |
| 3,585,995 | 6/1971 | Perkins | 128/214 R |
| 3,662,752 | 5/1972 | Yokoyama | 128/214 R |
| 3,747,769 | 7/1973 | Brumfield | 210/DIG. 23 |
| 3,814,258 | 6/1974 | Ayres | 210/DIG. 23 |
| 3,896,733 | 7/1975 | Rosenberg | 128/214 R |
| 3,901,808 | 8/1975 | Bokros | 128/214 R |

*Primary Examiner*—G.E. McNeill
*Attorney, Agent, or Firm*—Stanley N. Garber; William R. O'Meara

[57] ABSTRACT

An autotransfusion set includes a housing having a blood filtering and defoaming chamber connected to receive blood from a patient, and a blood reservoir connected to receive blood from the chamber and having an outlet for returning the blood to the patient, the blood normally being returned under pressure to increase the rate of infusion. A pressure relief valve is connected to the housing which has discrete, selectable pressure settings to limit the pressure within the chamber to a desired value. A float valve is disposed in the reservoir for closing it to the outlet when the blood level reaches a predetermined minimum level so as to preclude the infusion of air emboli to the patient, and for opening the reservoir to the outlet after the blood level has risen above the minimum level in order to reestablish infusion.

26 Claims, 3 Drawing Figures

AUTOTRANSFUSION DEVICE

BACKGROUND OF THE INVENTION

This invention relates to infusion devices and more particularly to an improved autotransfusion device.

The term "autotransfusion", as used herein, refers to the infusion of a patient's own blood back into the patient. For example, during certain types of cardiac surgery, an extracorporeal circulating system is used which has a blood pump and blood oxygenator for assuming the functions of the heart and lungs. In such a system, the patient's blood is continuously reinfused. Also, during certain types of surgery, it is highly desirable to return the patient's own blood that would otherwise be lost, especially where the blood loss would be relatively great.

In the latter case, an autotransfusion set is generally used which has blood filtering and reservoir chambers, a suction device and pump for picking up the blood and supplying it to the filtering chamber, and an outlet at the reservoir chamber which is connected to a hypodermic cannula to return the filtered blood to the patient. While the pump must be continuously operated to provide a sufficient suction force for drawing blood from the suction tip into the filtering chamber, the pressure in the chamber should be limited to only that necessary to obtain an adequate rate of infusion to avoid undesirable effects on the patient from too high a pressure. In some cases, a pressure relief tube is connected between the filtering chamber and a control valve located in a monitoring console, which console may also include the control for the pump as well as other devices. This arrangement has the disadvantages of requiring an additional tube and its connections, additional set-up time, and, in general, complicating the apparatus. Also, an autotransfusion set of the type having a relief tube can only be used where equipment having a pressure control device connectable with the tube is available.

When the autotransfusion set is used to return blood loss during surgery, the rate of flow of blood into the autotransfusion set chamber varies considerably, for example, it can vary from zero to a relatively high rate of flow. For this reason, it has generally been found necessary to have an attendant continuously monitor the apparatus to insure that the line into the patient is continuously filled with blood in order to avoid the infusion of air into the patient and air embolisms. When the blood level in the reservoir does reach a predetermined low level, it is necessary for the attendant to manipulate a control to close off the reservoir from the patient. Also, in some cases, the pressure control valve may fail to provide close regulation, and/or has parts such as springs and adjustable parts which are subject to malfunction.

SUMMARY OF THE INVENTION

Accordingly, it is an object of the present invention to provide an improved autotransfusion device wherein the above-mentioned disadvantages are substantially overcome.

More specifically, it is an object of the present invention to provide an autotransfusion device of the disposable type having improved pressure limiting means, automatic means for preventing air infusion, filtering and defoaming means, and a device which is relatively economical, safe, and simple to use.

In accordance with one form of the present invention, an autotransfusion device is provided which includes a housing having a filtering chamber for receiving and filtering blood from a patient, and a reservoir chamber connected with the filtering chamber and having an outlet for supplying filtered blood to the patient, and pressure limiting means on the device responsive to the pressure in one of said chambers for limiting the pressure therein.

These and other objects and advantages of the present invention will be apparent from the following detailed description and accompanying drawing.

DESCRIPTION OF THE PREFERRED EMBODIMENT

Figures 1, 2, 3:
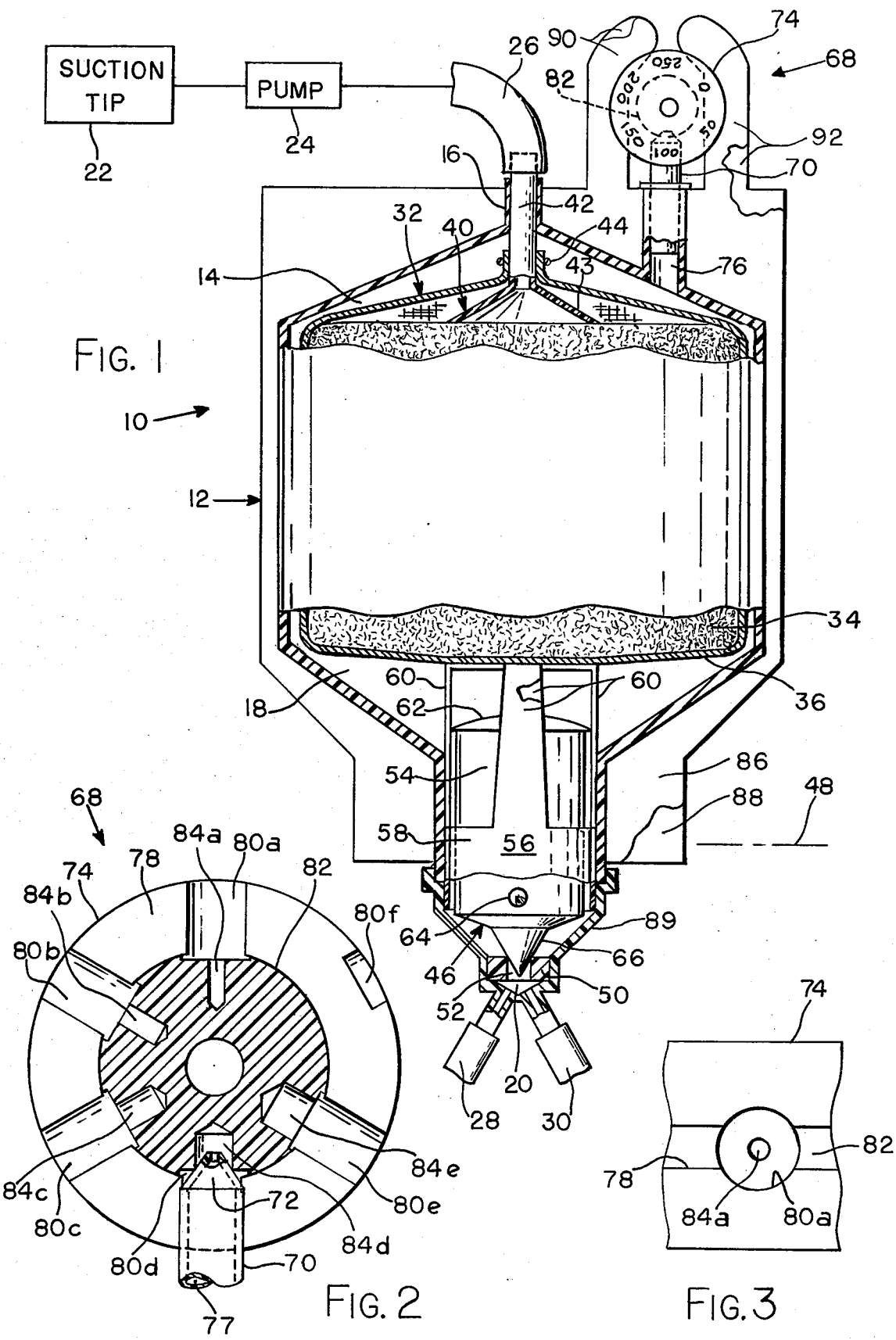
FIG. 1 is a cross-sectional elevational view of an autotransfusion device in accordance with a preferred embodiment of the invention.
FIG. 2 is a vertical cross-sectional view on an enlarged scale of a pressure limiting valve of the device of FIG. 1.
FIG. 3 is a fragmentary top plan view of the pressure limiting valve of FIG. 2.

Referring now to the drawing, and especially to FIG. 1, an autotransfusion device 10 is shown for illustration connected in an autotransfusion system in which a patient's own blood, which would otherwise be lost during surgery, is returned to that patient. As used herein, the term "patient" is intended to mean a human being or other animal.

The autotransfusion set 10 includes a housing 12 having an upper blood filtering chamber 14 having an inlet 16 at the top for receiving the patient's blood, and a lower reservoir chamber 18 in fluid communication with chamber 14 for receiving filtered blood. The reservoir chamber 18 has an outlet 20 for returning blood to the patient. A suction tip 22, which is generally held by an attendant for drawing up blood loss from the patient during an operation, is shown in block form connected to the suction side of a blood pump 24. Pump 24, which may be of the conventional roller type, has its positive pressure side connected to a blood inlet tube 26 which, in turn, is connected to the inlet 16 for supplying the blood to chamber 14. The outlet 20 is shown connected in fluid communication with a pair of blood outlet lines or return tubes 28 and 30 that are connected respectively to a pair of hypodermic cannulas (not shown) which are inserted into the veins of the patient. While the outlet 20 is shown supplying blood to a pair of return tubes, the outlet 20 may be constructed to supply only a single return tube where the infusion rate if adequate with a single tube.

Disposed in the upper chamber 14 is a filtering unit indicated generally at 32 which includes a blood defoaming member 34 and a filter 36 which entirely encloses the defoaming member. The defoaming member 34 may be made of any suitable blood defoaming material, preferably a preformed member of open-cell sponge material such as polyurethane sponge material that is coated throughout with an anti-foam agent such as silicone grease. The filter 36 is a fine mesh cloth, preferably a nylon filtering cloth, for example, a 100 micron nylon cloth. The filtering unit 32 includes a conduit 40, which may be of plastic, in the form of an inverted funnel having a tubular shank portion 42 sealingly secured such as by a tight friction fit or cement in the inlet 16 and which extends above the housing 12 to sealingly receive one end of blood inlet tube 26, the conduit serving as an inlet to the chamber 14. The funnel has a conical portion 43 with its widest end at the bottom which engages the upper end of the defoaming member 34. The filter 36 is shown in the form of a cloth bag having its open end closed against the tubular portion 42 of the conduit 40, the upper end of the bag being gathered around the tubular portion and secured thereto by a collar 44, such as a metal or plastic snap ring.

With this construction, connector 40 gently transfers blood from tube 26 directly to the defoaming member 34 since the connector extends through filter 36 and has its lower end in direct contact with the defoaming member 34. This insures that all blood passes through the defoaming member before flowing through the filter to the reservoir chamber 18. The defoaming member removes air bubbles or trapped air in the blood. After the blood passes through the defoaming member, all of it must then flow through the filter 36 before reaching the reservoir 18 so that all air and blood clots and debris are removed from the blood by the filtering unit 32 before it flows to the outlet 20. In the illustrated embodiment, the outer diameter of the filtering unit 32 is shown smaller than the inner diameter of the chamber 14 to permit blood to flow in the space between the side walls of the chamber and the filtering unit thus utilizing a relatively large area of the filter 36.

A float valve indicated at 46 is disposed at the bottom of the reservoir chamber 18 and is responsive to the level of blood in the reservoir chamber for shutting or sealing off the reservoir chamber from the outlet 20 and the patient when the blood level in the reservoir chamber drops to a predetermined minimum or safe level, such as indicated by a line at 48, and opens the reservoir chamber to the outlet when the blood level rises above level 48. Valve 46 serves as a shut-off valve and is shown including an annular valve seat 50 secured such as by a friction fit or cement to the bottom of the reservoir 18 forming an opening or passage 52, and a hollow, buoyant, float valve member 54 guided for movement toward and away from the valve seat by a guide or cage 56 secured in the reservoir chamber 18.

The valve guide 56, which may be a molded plastic part, has an annular lower portion 58 and four guide posts 60 extending vertically from the lower portion and connected together at the top. The filtering unit 32 is shown engaged and held in place between the funnel 40 and the top of guide 56.

The valve member 54 has an upper closure 62 having a peripheral flange which slidingly engages the four posts 60 to keep the upper end of the valve member centered during movement. Adjacent the lower end of the valve member 54 are three equally spaced, peripheral protrusions 64 (only one in view) which are slidable on the inner surfaces of the guide portion 58 to maintain the lower end of the valve member centered. A conical valve portion 66 at the bottom of the valve member 54 enters the valve seat opening 52 and sealingly engages the valve seat 50 to close the chamber 18 from the outlet 20 when the valve is in a closed position, the position illustrated in FIG. 1.

The valve member 54 may be made of any suitable plastic such as polycarbonate, cellulose acetate butyrate or polyurethane. The valve seat 50 may also be made of a suitable plastic material. Where the conical valve portion 66 is of relatively rigid material, the valve seat is preferably made of a soft, resilient material such as natural or synthetic rubber or a plastic such as a soft, resilient polyurethane material. The buoyancy of the valve member 54 is such that the valve member will move downwardly into sealing engagement with valve seat 50 to close the valve when the level of liquid or blood in the reservoir chamber drops to the minimum safe level, such as level 48 even when the pressure in the chamber 14 is at a minimum or zero value. The buoyancy of valve member 54 must also be great enough that the valve member will move upwardly away from the valve seat 50 to open the valve when the liquid or blood rises to some level above the minimum safe level 48 even when the pressure in the chamber 14 is at the maximum permissible operating value.

In order to insure that the fluid pressure in chambers 14 and 18 does not exceed a desired or preselected safe value regardless of the air and blood pressures produced in line 26 by pump 24, an adjustable pressure limiting or relief valve 68 is provided on the upper end portion of housing 12. Relief valve 68, as seen also in FIG. 2, includes a vertically extending tubular member or pintel 70 having a valve seat 72 at the upper end, and a relatively movable valve member or weight 74 disposed on pintel 70 and engageable with the valve seat 72, the valve seat supporting the weight of member 74. The pintel may be made of any suitable relatively hard plastic that will support the valve member 74.

The pintel 70 extends through the wall of housing 12 and is in fluid communication with the housing chambers 14 and 18. As seen in FIG. 1, pintel 70 is connected in sealing engagement, such as by a friction fit or by cement, in a vertically extending passage 76 having its lower end open to the filter chamber 14 adjacent the top of the chamber above the filtering unit 32. Thus, the pintel lumen, indicated at 77, is in direct fluid communication with the upper portion of chamber 14 at a point above the filtering unit 32 and above the blood flow path so that blood cannot enter it to clog the pintel. As seen in FIG. 1, the lower end of the pintel is above the lower end of passage 76 to further insure that no blood flows into the pintel lumen.

As seen in greater detail in FIGS. 2 and 3, the weight 74 of valve 68 is in the form of a disc or wheel which may be made of a suitable plastic such as polypropylene. The weight 74 is shown having a circumferential groove 78 extending entirely around its periphery, the width or axial dimension of the groove being less than the diameter of the pintel 70. A plurality of like recesses or passageways 80a–e are formed in the weight 74 such as by drilling radially into the groove 78 and slightly into a central hub portion indicated at 82, the recesses 80a–e being sized to slidingly receive the pintel 70. Recesses of different sizes, as indicated at 84a–e, are formed such as by driling further into the hub 82 respectively in aligned relation with the recesses 80a–e. The mouth or open end of each of the recesses 84a–e provides a valve seat for engagement with the valve seat 72 on pintel 70. As seen in FIG. 2, the weight 74 is positioned on pintel 70 with the pintel in recess 80d and with the mouth or seat of recess 84d sealingly engaging the pintel seat 72. In this position, the chamber 14 is closed off or not vented to atmosphere through valve 68. The valve seat 72 is shown conical and it and the upper open end of the pintel lumen 77 are, of course, sized to connect any of the recesses 84a–e in fluid communication with chamber 14.

Since the recesses 84a–e are of different sizes, each has a different pressure effective area so that the pressure required to lift or tilt the weight 74 away from the pintel valve seat 72 to open the valve will depend upon the recess used. The effective area of each of these recesses is the cross-sectional area of the particular recess. In the illustrated embodiment, the respective effective areas of the recesses 84a–e are constructed to provide maximum pressure settings of 50, 100, 150, 200 and 250 millimeters of mercury, respectively. Also, an additional recess 80f is formed by drilling only partially into groove 78 so that the pintel 70 supports the valve weight 74 but with the pintel seat 72 spaced from the hub 82 so that the filtering chamber 14 is continuously vented to atmosphere, this setting being a zero pressure setting for gravity feeding. As seen in FIG. 1, indicia in the form of numerals corresponding to these settings are imprinted on the face of member 74.

The housing 12 is economically formed of a suitable plastic material such as cellulose acetate butyrate, polycarbonate or the like. It is preferably formed of a relatively hard or rigid transparent plastic and may be constructed by thermoforming a pair of mirror image housing parts 86 and 88 which are connected together in face-to-face relation at their peripheries, and a cup-shaped molded plastic part 89 carrying valve seat 50 and providing connections for tubes 28 and 30. After the internal parts of the device are inserted, the housing parts may be cemented or solvent bonded together. The parts 86 and 88 are respectively provided with integral vertically extending arms 90 and 92 which are spaced apart a distance less than the diameter of the valve member 74 but greater than the diameter of the hub portion 82 so that the valve member may tilt and move up and down relative to the pintel 70. The upper ends of the arms 90 and 92 extend toward one another to limit the upper movement of the valve member 74. Arms 90 and 92 permit the valve member 74 to be manually raised off the pintel valve seat 72 to permit it to be rotated to any one of the selected positions or settings, that is, so that any one of the recesses 80a–f may be positioned to receive the pintel. The relatively rigid walls of passage 76, which are integral portions of the housing 12, support the weight of the movable valve member 74 which rests on pintel 70 in the passage. The pintel 70 is rigidly connected to housing 12 and may be an integrally connected part of housing 12 if desired. The pintel may be, for example, formed during the forming of the housing parts 86 and 88. Thus, housing parts 86, 88 and 89 form a unitary housing 12 carrying and supporting the filtering unit 32, blood level responsive valve 46, and the relief valve 68 to provide a compact autotransfusion device which is economical and simple to set-up and to use.

In operation, the autotransfusion set 10 is mounted in the vertical position as shown, for example, it may be secured in place by clamping the integral peripheral flange portion to a mast or fixture. The valve member 74 may be lifted off of the valve seat 72 of pintel 70 and rotated to the desired maximum pressure setting, for example, to the 100mm of mercury setting as indicated in the drawing. The device 10 may be primed with a suitable liquid such as blood or a saline solution. In some cases, the patient's own blood may be used to fill the lines 28 and 30 and the reservoir to at least a level 48 before the hypodermic cannulas are inserted into the patient in order to avoid infusion of air. With sufficient liquid or blood in the reservoir chamber, valve 46 will be in the open position. When the pump and suction tip are employed to return the blood loss of the patient during the surgical operation, blood will flow from the suction tip 22 into tube 26 and connector 40, the blood flowing gently from the funnel portion 43 into the defoaming member 34. Blood flows through the defoaming member and then through the filter 36 to the reservoir chamber 18. Some of the filtered blood will flow downwardly along the chamber walls and some will flow directly from the filter to the valve guide 56 since the guide is in direct engagement with the filter. With this construction, blood flows inwardly between the guide posts 60 and downwardly along the space between the guide 56 and valve member 54, and through open valve seat 50 to the outlet 20.

If the blood infusion rate is either too great because of excessive pumping pressures, or too low because the setting of relief valve 68 is too low, the manually operable valve member 74 is lifted and rotated to select a different maximum pressure setting that will permit a desired or adequate infusion rate. Should the liquid or blood level in reservoir chamber 18 fall to the predetermined minimum safe level 48, the float valve 46 will automatically close off the reservoir chamber to the outlet and patient to avoid air infusion. Whenever the blood level rises to a level above the level 48, the particular level depending upon the chamber pressure, the valve 46 will automatically open to allow blood flow from the reservoir chamber to the patient.

The autotransfusion device 10 of the present invention can be used where no other adequate pressure limiting device is available since the relief valve 68 is on the housing 12 in direct fluid communication with filter chamber 14. However, it can also be used advantageously in a system having another pressure limiting device since the valve 68 can then function as a safety or back-up limiting valve to provide protection in the event of a malfunction in the other pressure limiting device.

Since the minimum-level valve 46 of the present device operates automatically to properly close and open the reservoir chamber to the outlet, monitoring devices, such as photo detectors, for detecting a low level of blood in the reservoir or air in a line to the patient, are not required, or where used, the valve 46 provides for safe operation in the event the monitoring device fails. The use of valve 46 tends to eliminate or reduce human error where the monitoring of the blood is dependent on a person viewing the apparatus. Furthermore, no manipulation of controls is required to either open or close off communication between the reservoir and patient since valve 46 operates automatically. Also, because parts of the device 10 can be economically formed of plastic, the device can be of the disposable or single-use type.

While the reservoir chamber 18 may be in the form of a separate housing connected by a tube or the like to the filtering chamber 14, it is preferably formed by portions of the housing 12 such as is shown in the illustration. Also, the valve 56 is preferably disposed in the reservoir chamber 18, although it could be disposed in a separate housing in series between the filtering chamber and the patient.

It will now be apparent that all of the objects and advantages of the present invention hereinbefore mentioned, as well as others, are provided by the present invention. It should be understood that although this invention has been described with reference to the illustrated preferred embodiment, modifications thereto may be made without departing from the true spirit and scope of the invention.

What is claimed is:

1. An autotransfusion device comprising housing means including a filtering chamber having blood filtering means therein for receiving and filtering blood supplied thereto under pressure from a patient, and a reservoir chamber in fluid communication with said filtering chamber for receiving filtered blood therefrom and having an outlet for returning the filtered blood to the patient, and pressure limiting means on said housing means for limiting fluid pressure in said chambers including adjustable pressure relief valve means connected between one of said chambers and atmosphere and adjustable to selectively provide different pressure settings each limiting the fluid pressure in said one chamber to a different selected maximum value, said valve means being responsive to fluid pressure in said one chamber to vent said one chamber to atmosphere when the fluid pressure therein exceeds the maximum value of the selected setting and seal said one chamber from atmosphere when the fluid pressure therein is below the maximum value of the selected setting.

2. The device of claim 1 wherein said housing means comprises a unitary housing structure containing said filtering and reservoir chambers, and the weight of said pressure relief valve means is supported by said housing structure.

3. The device of claim 2 further including a shut-off valve in said reservoir chamber responsive to the level of blood therein for interrupting fluid communication between said reservoir chamber and said outlet when blood in said reservoir chamber falls to a predetermined minimum value.

4. The device of claim 1 including second valve means having a valve seat in said reservoir chamber at the outlet end thereof, and a buoyant valve member sealingly engageable with said valve seat in response to a predetermined low blood level in said reservoir chamber to close off the outlet from said reservoir chamber, said filtering means including blood filter and defoaming means, said pressure relief valve means being disposed above said blood filter and defoaming means and venting said filtering chamber at a location above said filter and defoaming means.

5. The device of claim 1 wherein said pressure settings are discrete settings, and said device has indicia thereon indicating the discrete settings.

6. The device of claim 1 wherein said pressure limiting means includes passage means extending through a wall of said housing means connecting an upper portion of said filtering chamber with the atmosphere, and said pressure relief valve means includes a movable valve menber mounted and supported by said housing means for movement from a position closing off said passage means and said filtering chamber from atmosphere to a position venting said passage means and said filtering chamber to atmosphere in response to a positive pressure in said filtering chamber above the selected maximum value corresponding to the selected pressure setting of said valve means for limiting the pressure in said filtering chamber.

7. The device of claim 1 further including second valve means in said reservoir chamber responsive to the level of blood therein to seal off said reservoir chamber from said outlet when the blood level therein reaches a predetermined minimum.

8. The device of claim 1 wherein said filtering means includes an open-cell defoaming member and a filter cloth substantially totally enclosing said defoaming member.

9. The device of claim 1 including a suction tip for drawing blood loss from a patient during surgery, a blood pump connected to transfer blood from said suction tip to said filtering chamber with the blood entering said filtering chamber under positive pressure, and means connecting said outlet with a vessel of the patient to return the blood loss to the patient.

10. The device of claim 1 further including pump means for delivering blood to said filtering chamber under positive pressure.

11. The device of claim 2 wherein said housing structure is substantially rigid plastic material.

12. The device of claim 6 wherein said passage means includes a vertically extending valve seat connected to said housing in fluid communication with said filtering chamber, and said movable valve member comprises a weight having an opening for sealingly receiving said valve seat closing off said passage means and filtering chamber from atmosphere, said weight being movable relative to said valve seat for venting said passage means and said filtering chamber to atmosphere to limit the pressure in said filtering chamber, said housing being substantially rigid to support said valve seat and said weight.

13. The device of claim 7 wherein said second valve means comprises a second valve seat at the outlet end of said reservoir, and a float valve member sealingly engageable with said second valve seat when the blood level in said reservoir chamber reaches said predetermined minimum.

14. The device of claim 8 including an inverted funnel having a cylindrical portion connected to receive the supplied blood and extending through said filter cloth, and a conical portion within said filter cloth with its widest end engaging said defoaming member.

15. The device of claim 8 wherein the upper end of said filter cloth is secured about said cylindrical portion of said funnel.

16. The device of claim 10 wherein said different pressure settings are discrete to provide corresponding discrete maximum values of positive pressure.

17. The device of claim 13 wherein said float valve member comprises a hollow plastic float having a specific gravity less than blood and has a conical lower end, and said valve seat has an annular opening for receiving said conical lower end in sealing engagement therewith.

18. The device of claim 17 further including a float guide for guiding said float valve member for axial movement toward and away from said second valve seat.

19. The device of claim 18 wherein said filtering means engages the upper end of said float guide.

20. An autotransfusion device comprising housing means including a filtering chamber having blood filtering means therein for receiving and filtering blood supplied thereto under pressure from a patient, and a reservoir chamber in fluid communication with said filtering chamber for receiving filtered blood therefrom and having an outlet for returning the filtered blood to the patient, and pressure limiting means on said housing means responsive to the fluid pressure in one of said chambers for limiting the pressure therein, said pressure limiting means including pressure relief valve means connected between said filtering chamber and atmosphere for venting said filtering chamber to atmosphere to limit the pressure therein to values below a predetermined value, said pressure relief valve means including an open-ended tubular pintel connected to and extending vertically from said housing in fluid communication with said filtering chamber, a valve seat at the upper end of said pinetl, and a weight having a plurality of spaced recesses each having an open end for receiving said valve seat in fluid sealing relation therewith, said weight being selectively positionable on said pintel to selectively position the open end of any one of said recesses in fluid sealing relation with said pintel, said recesses having different pressure effective areas whereby the maximum pressure permitted in said filtering chamber can be selected in accordance with the position of said weight relative to said pintel.

21. The device of claim 20 wherein said weight comprises a circular member with said recesses circumferentially spaced and extending radially inwardly, and said valve means being connected and supported by said housing.

22. The device of claim 20 wherein said weight comprises a circular member with said recesses circumferentially spaced and extending radially inwardly, and said valve means being connected and supported by said housing, said housing has a pair of spaced vertically extending guide members, and said weight has a circumferential groove and is disposed between said guide members with said groove receiving said guide members to secure said weight on said housing for limited movement relative thereto.

23. The device of claim 20 including second valve means having a second valve seat in said reservoir chamber at the outlet end thereof, and a buoyant valve member normally disposed in the blood in said reservoir chamber sealingly engageable with said second valve seat in response to a predetermined low blood level in said reservoir chamber to close off said outlet from said reservoir chamber, valve guide means connected to said housing means for guiding said buoyant valve member for movement toward and away from said second valve seat, said filtering means in said filtering chamber including a defoaming member of open-cell sponge and a filtering cloth substantially enclosing said defoaming member, said pintel communicating with said filtering chamber above said filtering means.

24. The device of claim 21 wherein said weight is of plastic material.

25. The device of claim 22 wherein at least one of said guide members has a portion extending generally horizontally over said weight to engage said weight and limit the upward movement thereof when lifted while permitting rotation of said weight between said guide members for moving said weight from one of said positions to another.

26. The device of claim 2 wherein said one chamber is said filtering chamber and said pressure relief valve means includes passage means extending through a wall of said housing structure for venting said filtering chamber to atmosphere, a valve seat rigidly connected to said housing structure at the end of said passage means, and a relatively movable valve member having a plurality of recesses of different pressure effective areas selectively engageable with said valve seat to provide said different pressure settings.

* * * * *